United States Patent
Sandal et al.

(10) Patent No.: US 7,145,058 B2
(45) Date of Patent: Dec. 5, 2006

(54) EFFICIENT METHOD OF PREVENTING GROWTH OF MICROBIAL GENETIC TRANSFORMANT AFTER TRANSFORMATION

(75) Inventors: Indra Sandal, Palampur (IN); Amita Bhattacharya, Palampur (IN); Ashu Gulati, Palampur (IN); Srigiripuram D. Ravindranath, Palampur (IN); Paramvir Singh Ahuja, Palampur (IN)

(73) Assignee: Council of Scientific and Industrial Research, New Delhi (IN)

( * ) Notice: Subject to any disclaimer, the term of this patent is extended or adjusted under 35 U.S.C. 154(b) by 381 days.

(21) Appl. No.: 10/106,528

(22) Filed: Mar. 27, 2002

(65) Prior Publication Data

US 2003/0186442 A1    Oct. 2, 2003

(51) Int. Cl.
*A01H 1/00*     (2006.01)
*A01N 65/00*    (2006.01)
*C12N 15/84*    (2006.01)

(52) U.S. Cl. ............ 800/294; 424/729; 435/469; 435/431

(58) Field of Classification Search .......... 800/294, 800/298; 424/195.1, 729; 435/469
See application file for complete search history.

(56) References Cited

OTHER PUBLICATIONS

Gerhardt et. al. (Manual of Methods for General Bacteriology, 1981, eds. Gerhardt et. al , American Society for Microbiology, Washington DC, pp. 476-482 and 484.).*
Yamamoto et. al. (Chemistry and Applications of Green Tea, 1997, eds. Yamamoto et. al., CRC Press, Boca Raton, pp. 1-151, especially Tables 1 and 2, pp. 2-3; Figure 3, p. 7; Tables 4-6, p. 8-9, and Tables 1 and 2, p. 14-15). p. 1-11, 13-19.*

* cited by examiner

*Primary Examiner*—David T. Fox
*Assistant Examiner*—Georgia Helmer
(74) *Attorney, Agent, or Firm*—Smith, Gambrell & Russell, LLP

(57) ABSTRACT

The present invention relates to an efficient and cost effective method of preventing growth of genetic transformant bacteria *Agrobacterium tumefaciens* after transformation in plants by using tea leaf extract as a bactericide, wherein said method leads to elimination of common problem of polyphenol oxidation during transformation and thereby helps maintain regeneration potential in explants and also helps in increased transformation efficacy

14 Claims, 1 Drawing Sheet

… continued

Figure 1:
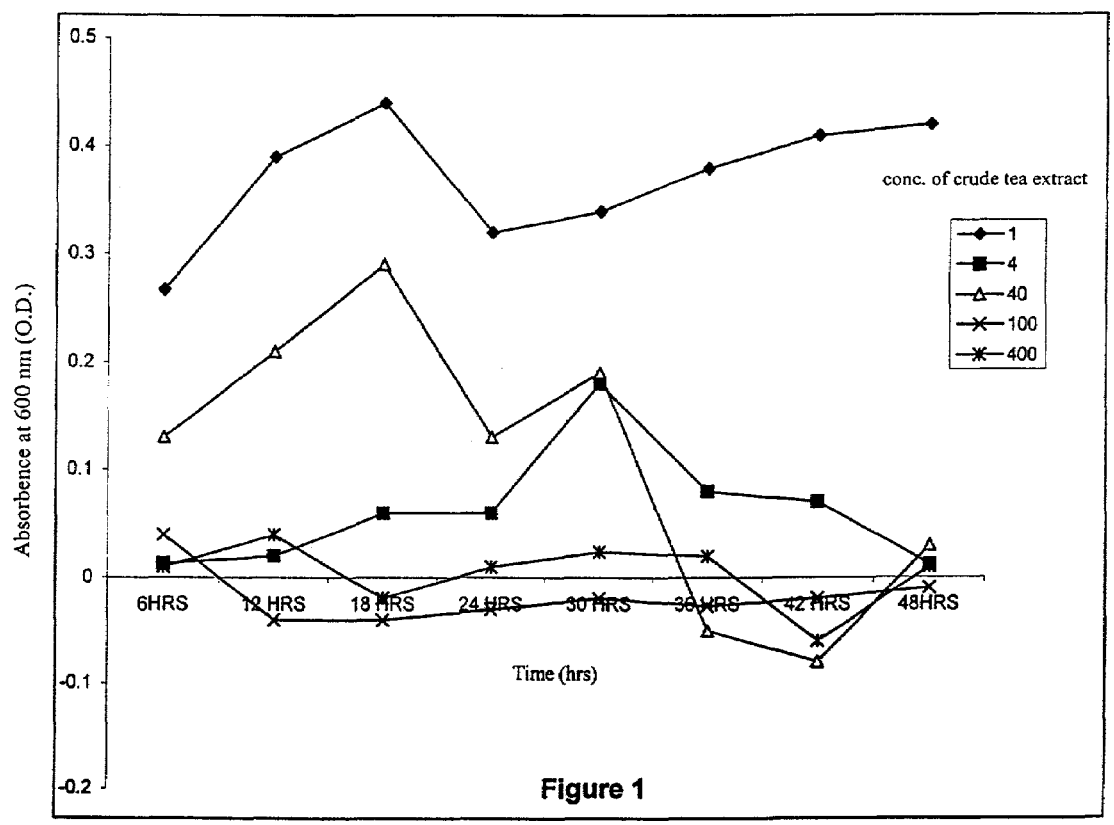

EFFICIENT METHOD OF PREVENTING GROWTH OF MICROBIAL GENETIC TRANSFORMANT AFTER TRANSFORMATION

FIELD OF THE INVENTION

The present invention relates to an efficient and cost effective method of preventing growth of genetic transformant bacteria *Agrobacterium tumefaciens* after transformation in plants by using tea leaf extract as a bactericide, wherein said method leads to elimination of common problem of polyphenol oxidation during transformation and thereby helps maintain regeneration potential in explants and also helps in increased transformation efficacy.

BACKGROUND AND PRIOR ART REFERENCES

'Transgenics' appear to be the 'need of the hour' in view of the ever growing demand for quality crops all over the world (Somerville C. R. 1994. In: Production and Uses of Genetically Transformed Plants, Chapman and Hall, London (eds. Bevan M. W., Harrison R. D., Leaver C. J.).

Transgenic production through genetic transformation of plants is brought about by introducing desired gene(s) from any living organism into the concerned plant by different methods of DNA delivery in order to impart different traits for crop improvement viz. disease and pest resistance, longer shelf life, better and added nutritional value, varied colours and scents, tolerance to abiotic stresses like drought, flood, cold, salt etc.

Of the different methods of gene delivery into plants, the most popular and cost effective method is producing transgenics through *Agrobacterium tumefaciens*. By this method explants that have the ability to regenerate into full grown plants under tissue culture conditions are infected with the disarmed and engineered strains of the soil bacteria '*Agrobacterium tumefaciens*' containing the desired engineered genes.

Once the infection has occurred, the virulence genes of the *Agrobacterium tumefaciens* gets triggered and this enables the bacterium to pass on the T-DNA containing the desired engineered gene into the plant cell/nucleus and finally the desired engineered gene gets integrated into the plant genome which then becomes genetically transformed.

For successful and high frequency of genetic transformation of plants, fresh actively growing cultures of *Agrobacterium tumefaciens* containing the engineered and disarmed T-DNA is generally grown for 12–16 hr at 25–30° C. and 150–200 rpm in dark upto its log phase of growth when the cell density becomes $1 \times 10^9$ cells/ml. The explants are then infected with these fresh cultures and allowed to incubate for a few days at optimal temperature and pH so that the T-DNA with the desired engineered gene is passed on to plant cell/nucleus which finally gets integrated into the plant genome. Once the gene is integrated either transiently or stably into plant genome, the residual *Agrobacterium tumefaciens* needs to be eliminated totally or else the residual *Agrobacterium* overgrows on the explant and prevents it from regenerating into a healthy plant and in severe cases even kills the explants.

A serious drawback of *Agrobacterium tumefaciens* mediated genetic transformation protocols is the requirement of high cost and labour intensive steps of washing and subsequent repeated culturing of transformants onto a medium containing expensive bactericidal antibiotics in order to kill *Agrobacterium tumefaciens*. These repeated washings and sub-culture involving bactericidal antibiotics not only result in vitrification of the transformants but also in their loss due to severe bacterial overgrowth. The problem is so severe that about 50% of the transformants are lost due to bacterial overgrowth and many a times, the generally employed bactericidal antibiotics fail to prevent this loss at feasible doses.

In a preliminary study, crude leaf extracts were found to have a bactericidal effect on the overgrowing *Agrobacterium tumefaciens* after co-cultivation, yet another important problem that was encountered was the loss and death of transformants due to phenol oxidation. It was therefore, necessary to optimize a concentration or composition of tea leaf extract that would not only kill the residual *Agrobacterium tumefaciens* after the transfer and integration of its T-DNA into the plant genome but would also overcome the problem of loss and death of the explants due to phenol oxidation.

Tea leaves contain high levels of polyphenols which are composed of 6 types of catechins (C) and their derivatives viz., epicatechin (EC), gallocatechins (GC), epigallocatechins (EGC), epicatechin gallate (ECg), epigallocatechin gallate (EGCg). Besides polyphenols, tea leaves also contain caffeine, amino acids and other nitrogenous compounds, vitamins, inorganic elements, carbohydrates and lipids (Chu D-C and Juneja L. R. General chemical composition of green tea and its infusion. In: Chemistry and Application of Green Tea. 1997. CRC Press, N.York. eds. Yamamoto T., Juneja L. R., Chu D-C, Kim M.). Tea polyphenols are known to show several biochemical activities such as inhibition of bacterial mutation (Kada T., Kaneka K., Matsuzaki T. and Hara Y. 1985. Detection and chemical identification of natural biomutagens. A case of green tea factor. *Mutation Research* 150: 127), inhibition of HIV reverse transcriptase activity (Nokane H. and Ono K. 1990. Differential inhibitory effects of some catechins derivatives on the activities of human immunodeficiency virus reverse transcriptase and cellular deoxyribonucleic and ribonucleic acid polymerases, *Biochemistry* 29: 2841–5).

Tea polyphenols have shown anticaries effects by inhibiting the adherence of *P. gingivalis* onto buccal epithelial cells at concentrations 250–500 µg/ml which is much larger compared to the effective concentrations of antibiotics (Sakanaka S., Aizawa M., Kim M. and Yamamoto T. 1996 Inhibitory effects of green tea polyphenols on growth and cellular adherence of an oral bacterium *Porphyromonal gingivalis*. *Biosci. Biotechnol. Biochem.* 60: 745; Sakanaka S. 1997. Green tea polyphenols for prevention of dental caries In: Chemistry and Application of Green Tea. eds. Yamamoto T., Juneja L. R., Chu D-C, Kim M.). Tea polyphenols have also been reported to possess antiviral activity dependent on the galloyl moiety linked by ester linkage in catechin molecule (John T. J. and Mukundan P. 1979.

Virus inhibition by tea, caffeine and tannic acid. *Indian J. Med. Res.* 69: 542; Nakayama M., Toda M., Okubo S. and Shimamura T. 1990. Inhibition of influenza virus infection by tea. *Lett. Appl. Microbiol.* 11: 38). Huang and Frankel, 1997 (Huang S-W and Frankel E. N. 1997 Antioxidant activity of tea catechins in different lipid systems. *J. Agric. Food Chem.* 45: 3033–8) have reported antioxidant activity of tea catechins in liposomes. Also tea catechins have been reported to scavenge the oxidative radicals that cause damage to the DNA (Yen G-W. and Chen H-Y. 1995. Antioxidant activity of various tea extracts in relation to their antimutagenecity. *J. Agric. Food Chem.* 43: 27–32), and their oxygen radical absorbing action with antiproliferative action in human epidermoid carcinoma A431 cells (Lin Y-L., Juan I-M., Chen Y-L., Liang Y-C. and Lin J-K. 1996. Composition of polyphenols in fresh tea leaves and associations of their oxygen-radical-absorbing capacity with antiproliferative actions in fibroblast cells. *J. Agric. Food Chem.* 44: 1387–94).

Saeki et al. 1999 (Saeki K., Sano M., Miyase T., Nakamura Y., Hara Y., Aoyagi Y. and Isemura M. Apoptosis-inducing activity of polyphenol compounds derived from tea catechins in human histiolytic lymphoma U937 cells. *Biosci. Biotechnol. Biochem.* 63: 585–7) have recorded the apoptosis inducing activity of polyphenols of tea as evidenced by inhibition of DNA ladder formation and chromatin condensation in human histiolytic lymphoma cells. Antimicrobial activity of green tea extract has also been well documented at minimum inhibitory concentration or MIC (250 μg/ml to 1000 μg/ml) for several micro-organisms that are harmful to human health (In: Chemistry and Application of Green Tea. 1997. CRC Press, New York. eds. Yamamoto T., Juneja L. R., Chu D-C, Kim M.). Crude tea leaf extract thus, appears to be a potent agent for bactericidal formulations during genetic transformation, once the problem of phenolic oxidation and hence death of the transformants is alleviated.

One of the problems encountered during plant tissue transformation with *A. tumefaciens* is the effective elimination of the bacterium after transfer of the transgenes has taken place. When using *Agrobacterium* as a tool in plant genetic engineering, there is a risk that if not all bacteria are eliminated after transformation, the residual bacteria will kill the transgenic plants. Therefore, strategies in genetic transformation generally require a balance between the bactericidal activity and the normal morphogenetic response of transformed tissue. Different reports on these problems include the report by Colby and Meredith (Colby S. M. and Meredith C. P. Kanamycin sensitivity of cultured tissues of *Vitis Plant Cell Reports* 9(5): 237–40) who used the bactericidal antibiotic carbenicillin for killing residual *Agrobacterium tumefaciens* during genetic transformation but the drawback of their report was that carbenicillin had inhibitory effects on plant regeneration which sometimes resembled those of growth inhibitors.

Also, Park et al., 1990 (Park Y. G., Shin D. W., Kim J. H. 1990. *Journal of Korean Forestry Society* 79(3): 278–84) used a combination of cefotaxime (200 mg/liter) and carbenicillin (300 mg/liter) for *Agrobacterium* mediated transformation of *Populus nigra X P. maximowiczii* leaves. The drawback of the protocol was that although, the growth of *Agrobacterium tumefaciens* strain 6044 was reduced, yet, the residual *Agrobacterium tumefaciens* was not totally eliminated and the rate of regeneration was also as low as 10%.

Yurkova et al., 1993 (Yurkova G. N., Chugunkova T. V. and Shevtsov I. A. 1993. Effect of antibiotics on the tissue culture of sugarbeet and fodder beet. *Tsitologiya-i-Genetika* 27(2): 3–6) used a combination of claforan and carbenicillin as inhibitors of *Agrobacterium* cells during transformation of diploid sugarbeet hybrid and 2 diploid varieties of fodder beet. However, the drawback of this report was that this combination had an inhibiting effect on shoot formation.

Yepes and Aldwinckle, 1994 (Yepes L. M. and Aldwinckle H. S. 1994. Micropropagation of thirteen *Malus* cultivars and rootstocks, and effect of antibiotics on proliferation. *Plant Growth Regulation* 15(1): 55–67) used cefotaxime at 200 mg/liter and carbenicillin at 500 mg/liter for the transformation of 13 apple cultivars. However, the drawback of the report was that while cefatoxime caused abnormal shoot morphology, carbenicillin alone or in combination with cefotaxime at 200 mg/liter, inhibited proliferation and caused excessive enlargement of the basal leaves, inducing callus formation and release of phenolic compounds in the medium. Lin et al., 1995 (Lin-J J., Assad-Garcia N. and Kuo, J. 1995.

Plant hormone effect of antibiotics on the transformation efficiency of plant tissues by *Agrobacterium tumefaciens* cells. *Plant Science Limerick.* 109(2): 171–177) reported the use of 250 to 2000 μg/ml carbenicillin for the inhibition of bacterial (*A. tumefaciens* strains, LBA4404, C58 and EHA101) growth in tobacco leaf explants wherein they showed that LBA4404 was the most sensitive to carbenicillin and cefotaxime. However, the drawback of the protocol was that the regeneration efficiency from leaf explants decreased with the addition of increasing concentration of carbenicillin on MS medium containing 0.5 μg/ml of benzyladenine and/or 2,4-D wherein they emphasized on the toxic effects on leaf explants when grown on MS medium containing a combination of 250 μg/ml carbenicillin and 1 μg/ml 2,4-D due to the auxin related chemical structures of 2,4-D or NAA and carbenicillin. The major drawback of this protocol is that such plant growth regulators (2,4-D, BA or NAA) are generally used in most regeneration media that are employed for *Agrobacterium tumefaciens* mediated transformation.

Sarma et al, 1995 (Sarma K. S., Evans N. E. and Selby C. 1995. Effect of carbenicillin and cefotaxime on somatic embryogenesis of Sitka spruce (*Picea sitchensis* (Bong.) Carr. *Journal of Experimental Botany* 46(292):, 1779–81) reported the use of antibiotics viz. carbenicillin and cefotaximethese in an attempt to transform Sitka spruce somatic embryos using *Agrobacterium* based vectors. They reported that carbenicillin should not be used for transformation of Sitka spruce. The drawback of the report was that carbenicillin prevented the development of mature somatic embryos, reduced early stage embryos by >90% and tissue growth by 50%.

Cefotaxime had no effect on overall tissue growth, but reduced the development of early and mature embryos by 20% and 66–80%, respectively.

Shackelford and Chlan 1996 (Shackelford N. J. and Chlan C. A. 1996. Identification of antibiotics that are effective in eliminating *Agrobacterium tumefaciens*. *Plant Molecular Biology Reporter* 14(1): 50–5) performed an assay using ten antibiotics viz. cefotaxime, carbenicillin, erythromycin, spectinomycin, polymixin B, chloramphenicol, methicillin, augmentin 500, augmentin 250 and moxalactam [latamoxef] inorder to identify the antibiotics that are most effective against *A. tumefaciens* strains EHA101 and LBA4404, and to determine if these antibiotics inhibited tobacco callus and shoot formation. This report indicates that a major drawback of most transformation protocol is time consuming assays involving several costly antibiotics for the effective elimination of *A. tumefaciens* after gene transfer into plant explant has taken place.

Barrett et al., 1997 (Barrett C., Cobb E., McNicol R. and Lyon G. 1997 A risk assessment study of plant genetic transformation using *Agrobacterium* and implications for analysis of transgenic plants. *Plant Cell Tissue and Organ Culture.* 47(2): 135–44) examined *Agrobacterium* transformation systems for *Brassica, Solanum* and *Rubus*, using carbenicillin, cefotaxime and ticaracillin [ticarcillin], respectively, to eliminate contamination, for the presence of residual *Agrobacterium*. Results indicated that none of the antibiotics tested succeeded in eliminating *Agrobacterium* and the contamination levels increased in explants from 12 to 16 weeks to such an extent that *Solanum* cultures senesced and died. This may be due to the fact that in some cases the minimum bactericidal concentration values (concentration to be used for elimination of contaminants in culture) for the three antibiotics were higher than the concentrations employed in the culture medium.

Moreover, even up to 6 months after transformation, 50% of contaminated material still harboured bacterial cells with the binary vector at levels of 107 colony forming units per gram. This report indicates a major drawback with most of the generally used antibiotics are ineffective for *Agrobacterium* elimination in plants like *Brassica, Solanum* and *Rubus* and affects their regeneration as well as survival efficiency.

Hammerschlag et al., 1997. (Hammerschlag F. A., Zimmerman R. H. Yadava, U. L., Hunsucker S. and Gercheva P. 1997. Effect of antibiotics and exposure to an acidified medium on the elimination of *Agrobacterium tumefaciens* from apple leaf explants and on shoot regeneration. *Journal of the American Society for Horticultural Science.* 122(6): 758–63) tested a range of antibiotics and their short-term exposure to an acidified (pH 3.0) medium for their effects on eliminating *A. tumefaciens*, supervirulent strain EHA101 (pEHA101/pGT100), on leaf explants of Royal Gala apples (Malus domestica [*M. pumila*]) and on shoot regeneration.

They reported that the exposure of leaf explants to regeneration and elongation media containing 100 µg/ml of the antibiotics carbenicillin (crb), cefotaxime (cef), and cefoxitin (mefoxin (mef)), singly or in combination for 52 days, did not eliminate *A. tumefaciens* from the explants. The drawback of this report was that even short-term (1 to 18-hour) vacuum infiltration with 500 µg/ml of any of the antibiotics did not inhibit regeneration and failed to completely eliminate *A. tumefaciens* from leaf explants.

Cheng et al., 1998 (Cheng, Z. M., Schnurr, J. A. Kapaun, J. A. 1998. Timentin as an alternative antibiotic for suppression of *Agrobacterium tumefaciens* in genetic transformation. *Plant Cell Reports* 17(8): 646–9) studied the effects of timentin on shoot regeneration of tobacco (*Nicotiana tabacum*) and Siberian elm (*Ulmus pumila*) and its use for the suppression of *Agrobacterium tumefaciens* during genetic transformation. Timentin—a mixture of ticarcillin and clavulanic acid was used effectively at concentrations of 200–500 mg/l and at ratios of ticarcillin:clavulanic acid at 50:1 and 100:1. The drawback of this report is that although timentin is a less expensive alternative to the use of carbenicillin or cefotaxime antibiotics for the effective suppression of *A. tumefaciens* after genetic transformation yet it is expensive synthetic antibiotic as compared to natural agents like crude tea extracts.

Ling et al., 1998 (Ling H. Q., Kriseleit D. and Ganal M. W. 1998. Effect of ticarcillin/potassium clavulanate on callus growth and shoot regeneration in *Agrobacterium* -mediated transformation of tomato (*Lycopersicon esculentum* Mill.) *Plant Cell Reports* 17(11): 843–7) studied the effect of Cefotaxime, ticarcillin/potassium clavulanate on tomato transformation. Cefotaxime did not inhibit callus growth in culture medium, but it clearly decreased shoot differentiation. While cefatoxime showed a strong negative effect on callus growth, shoot regeneration and transformation efficiency, the ticarcillin/potassium clavulanate was more economical and effective than carbenicillin and cefotaxime. The drawback of the report is that although ticarcillin/potassium clavulanate was a very good alternative to eliminate *Agrobacterium tumefaciens* in plant transformations yet it is an expensive synthetic antibiotic as compared to natural agents like crude tea extracts.

Joersbo et al. 2000 (Joersbo M., Brunstedt, J. Marcussen, J. Okkels F. T. 2000. Transformation of the endospermous legume guar (*Cyamopsis tetragonoloba* L.) and analysis of transgene transmission. *Molecular-Breeding* 5(6): 521–9) used carbenicillin and cefotaxime, for the elimination of *Agrobacterium* after co-culture, wherein they found considerable toxicity was displayed to guar tissues due to beta-lactams. When the beta-lactams were replaced by the non-phytotoxic beta-lactamase inhibitor "sulbactam" alongwith thidiazuron and silver thiosulfate the problem was overcome. The drawback of this report was that while the commonly used carbenicillin and cefotaxime were phytotoxic to the explants used, replacement of beta-lactams by sulbactam is a costly process.

OBJECTS OF THE PRESENT INVENTION

The main object of the present invention is to develop a method is to use tea leaf extract for killing the overgrowth of *Agrobacterium tumefaciens* in systems or plants or explants requiring longer co-cultivation periods in order to increase the transformation efficiency. Moreover, the crude tea extract is able to eliminate the risk of residual *Agrobacterium* released along with the transgenic plants thereby maintaining a balance between the selection pressures and the normal morphogenetic response.

Another object of the present invention is the use of tea leaf extract for *Agrobacterium tumefaciens* genetic transformation in different systems or plants or explants wherein the generally used bactericidal antibiotics are ineffective.

Further object of the present invention is to develop a method to enhance the transformation efficacy of the bacteria *Agrobacterium tumefaciens*.

Another object of the present invention is to develop a method to prevent polyphenol oxidation involved with such kind of transformation.

Yet another object of the present invention is to develop a method wherein normal growth of the transformed plant is not affected by the this mode of transformation involving bacteria *Agrobacterium tumefaciens*.

Yet another object of the present invention is to develop a cost-effective system for *Agrobacterium tumefaciens* genetic transformation wherein no commercial and yet costly antibiotics are used.

Still another object of the present invention is to develop an economical system for obtaining the bactericidal agent without involving any costly extraction methods wherein the crude leaf extract with bactericidal activity is extracted without requiring expensive instruments.

Still another object of the invention is to develop a method wherein a crude leaf extract with bactericidal activity can be obtained in abundance from naturally growing tea bushes.

Still another object of the present invention is to develop a method wherein the bactericidal agent is of natural origin and is not of synthetic or semi-synthetic nature.

Still another object of present invention is to develop a method wherein, the bactericidal agent can be obtained in abundance from actively growing two and a bud making it economical.

Still another object of the present invention is to develop a method wherein, the bactericidal agent can be obtained in abundance from even the lower maintenance foliage thereby making it more economical as generally such leaves are discarded or burnt.

Still another object of the present invention is to develop a method wherein, the crude leaf extract can also be used as a bactericidal agent for other contaminating bacteria in different in vitro systems involving different plants or explants.

Still another object of the present invention is to develop a method wherein, the crude extract can also be used during 'hairy root production' using *Agrobacterium rhizogenesis*.

Still another object of the present invention is to develop method wherein the transformation efficiency can be increased considerably by decreasing the mortality rate of transformants due to *Agrobacterium* overgrowth.

Further object of the present invention is to obtain tea leaf extract having bactericidal property for *Agrobacterium tumefaciens* mediated genetic transformations which obviates the drawbacks as detailed above.

SUMMARY OF THE PRESENT INVENTION

The present invention relates to an efficient and cost effective method of preventing growth of genetic transformant bacteria *Agrobacterium tumefaciens* after transformation in plants by using tea leaf extract as a bactericide, wherein said method leads to elimination of common problem of polyphenol oxidation during transformation and thereby helps maintain regeneration potential in explants and also helps in increased transformation efficacy.

DETAILED DESCRIPTION OF THE PRESENT INVENTION

In an embodiment of the present invention, an efficient and cost effective method of preventing growth of genetic transformant bacteria *Agrobacterium tumefaciens* after transformation in plants by using tea leaf extract as a bactericide.

In another embodiment of the present invention, inoculating said bacteria harbouring antibiotic resistant genes and reporter gus gene in a culture medium with said antibiotics.

In yet another embodiment of the present invention, incubating the said culture in dark.

In still another embodiment of the present invention, harvesting the cells during log phase.

In still another embodiment of the present invention, pelleting live bacterial cells.

In still another embodiment of the present invention, suspending the said pellet in fresh culture medium.

In still another embodiment of the present invention, optimizing the cells density.

In still another embodiment of the present invention, immersing various explants of different plants in bacterial suspension.

In still another embodiment of the present invention, removing excess bacteria from explant.

In still another embodiment of the present invention, incubating explant in media for different time durations.

In still another embodiment of the present invention, preparing crude extract of tea leaf to be used as bactericide by drying leaves.

In still another embodiment of the present invention, preparing acetone extract overnight.

In still another embodiment of the present invention, filtering the extract.

In still another embodiment of the present invention, extracting filterate with n-hexane to obtain aqueous and lipid layers.

In still another embodiment of the present invention, concentrating aqueous layer to dryness.

In still another embodiment of the present invention, diluting concentrated extract using with water to obtain crude tea extract.

In still another embodiment of the present invention, estimating total catechins and caffeine in said extract.

BRIEF DESCRIPTION OF THE ACCOMPANYING DRAWINGS

FIG. 1 shows effect of varying concentration (1, 4, 40, 100, and 400 µg/ml) of crude tea extract on the growth of *Agrobacterium tumefaciens*. The growth of said bacteria is inhibited with increasing concentration of the tea extract. The growth of bacteria is measured spectrophotometrically. The variation of growth is measured for up to 48 hours at an interval of 6 hours each.

In still another embodiment of the present invention, transferring explants of various plants into medium containing various concentrations of 0–600 µg/ml of crude extract (FIG. 1) and catechin and caffeine fractions separately.

In still another embodiment of the present invention, obtaining bacteria free transgenic explants.

In still another embodiment of the present invention, wherein antibiotics are selected from a group comprising Kanamycin, and hygromycin.

In still another embodiment of the present invention, wherein culture medium is yeast mannitol broth.

In still another embodiment of the present invention, wherein concentration of bacteria is ranging between 10 to 75 micrograms/ml.

In still another embodiment of the present invention, wherein incubating culture at temperature ranging between 20 to 35° C.

In still another embodiment of the present invention, wherein incubating culture at revolution rate ranging between 100 to 300 rpm for time duration ranging between 10 to 20 hours.

In still another embodiment of the present invention, wherein harvesting the said culture at optical density ranging between 0.6–0.8 at 600 nm for concentration of about $1 \times 10^9$ cells/ml.

In still another embodiment of the present invention, wherein pelleting the harvest by centrifuging at 3000–9000 rpm for about 20 to 40 minutes.

In still another embodiment of the present invention, wherein centrifuging said culture at temperature ranging between 20 to 35° C.

In still another embodiment of the present invention, wherein cell density is measured spectrophotometrically.

In still another embodiment of the present invention, wherein cell density is measured by estimating optical density after about every 6 hours interval to estimate growth rate of said bacteria spectrophotometrically.

In still another embodiment of the present invention, wherein optimization of cell density has O.D. ranging between 0.6 to 0.8 at 600 nm at $1 \times 10^9$ cells/ml upto 60 hours.

In still another embodiment of the present invention, wherein immersing said tea explant in bacterial suspension for time duration ranging between 3 to 40 minutes.

In still another embodiment of the present invention, wherein removing excess bacteria from explant by blotting of explant on filter paper.

In still another embodiment of the present invention, wherein co-cultivating explant for time duration ranging between 1 to 20 days.

In still another embodiment of the present invention, wherein concentration of tea plant extract is ranging between 1 to 1000 micrograms/ml.

In still another embodiment of the present invention, wherein leaves are dried in oven at temperature ranging between 50 to 70° C.

In still another embodiment of the present invention, wherein acetone is at concentration ranging between 5 to 50%.

In still another embodiment of the present invention, wherein acetone extract is prepared at room temperature.

In still another embodiment of the present invention, wherein concentrating aqueous layer to drying using rotary evaporators.

In still another embodiment of the present invention, wherein ratio of acetone and n-hexane is ranging between 4:5 to 12:1.

In still another embodiment of the present invention, wherein concentration of tea leaf extract in acetone solution is in the ratio ranging between 200 to 500 gms/L.

In still another embodiment of the present invention, wherein concentration of catechins and caffeine is ranging between 2 to 750 micrograms/ml in culture.

In still another embodiment of the present invention, wherein using tea extract as bactericide eliminates the problem of polyphenol oxidation.

In still another embodiment of the present invention, wherein said plants show normal growth after using tea extract as bactericide.

In still another embodiment of the present invention, wherein said method shows increased transformation efficacy.

In still another embodiment of the present invention, wherein the transformation efficiency can be increased considerably by decreasing the mortality rate of transformants due to *Agrobacterium* overgrowth.

In further embodiment of the present invention, the method of transformation used in the instant application employing bacteria *Agrobacterium tumefaciens* causes no polyphenol oxidation. The polyphenol oxidation usually affects the normal growth of the transformed plant in such kinds of transformation in plants. But, use of tea leaf extract as a bactericide after transformation of plant by said bacteria facilitate normal growth of the transformed plant.

In another embodiment of the present invention, transformation efficacy facilitated by the said bacteria rises on the use of tea leaf extract as a bactericide for *Agrobacterium tumefaciens*. The said extract decreases the mortality rate of transformant due to bacterial overgrowth.

In further embodiment of the present invention, tea leaf extract as a potent bactericidal agent for *Agrobacterium tumefaciens* mediated genetic transformations which comprises (i) inoculation of two strains of *Agrobacterium tumefaciens* viz. EHA105 (mild) and GV2260 (virulent) harbouring the antibiotic resistance genes for kanamycin or hygromycin and the reporter gus gene from mother cultures of respective strains into 10–30 ml liquid modified Yeast Mannitol Broth with kanamycin or hygromycin (ii) incubation for 12–16 hr at 25–30° C. and 150–200 rpm in dark (iii) harvesting at 0.6–0.8 optical density at 600 nm for $1 \times 10^9$ cells/ml during log phase of bacterial growth (iv) pelleting of living bacterial cells by centrifugation at 15–30 minutes at 4000–8000 rpm and 25–30° C. (v) suspension of bacterial pellet in fresh 5–25 ml of Yeast Mannitol Broth without damaging the bacterial cells (vi) optimization of bacterial cell density at $1 \times 10^9$ cells/ml by measuring optical density at 600 nm (vii) immersion of various explants of different plants in bacterial suspension for 5–35 minutes (viii) blotting of explants on filter papers to remove excess *Agrobacterium tumefaciens* (ix) incubation of explants on incubation medium for different periods of 1–10 days (x) preparation of crude extract of tea leaf to be used as a bactericidal agent by drying 100–500 g fresh tea leaves of Kangra jat in an oven at 60° C. (xi) overnight extraction of dried leaves at room temperature with 0.4–1.2 liters of 10–40% aqueous acetone and filteration (xii) extraction of the filtrate with 100–500 ml of n-hexane to obtain two layers for removal of lipids (xiii) the aqueous layer taken and concentrated to dryness using standard rotary evaporators (xiv) concentrated extract diluted with water to 10–50 ml and total catechins and caffeine estimated (xv) the aqueous extract served as a crude mixture (xvi) transfer of various explants of different plants to regeneration medium containing different concentrations of 0–600 µg/ml crude tea extract and catechin and caffeine fractions separately for totally killing the residual *Agrobacterium tumefaciens* and for eliminating the problem of polyphenol oxidation in the explants in order to maintain the regeneration potential of explants (xi) transfer of *Agrobacterium tumefaciens* free explants to regeneration medium containing selection antibiotics for further regeneration and transgenic plant development (xii) optimization of the concentration and fractions of tea leaf extract on the growth curve of *Agrobacterium tumefaciens* in both solid and liquid Yeast Mannitol Broth media in order to determine the optimum concentration for desired bactericidal activity as well as for promoting regeneration potential of the explant.

In further embodiment of the present invention, different explants of different plant species were used for transgenic production.

In yet another embodiment of the present invention, different concentrations of filter sterilized and autoclaved de-caffeinated fractions of catechin were added as above.

In still another embodiment of the present invention, different concentrations of D-catechin of *Acacia* species were used as mentioned above wherein D-catechin was found to promote and not inhibit the growth of *Agrobacterium tumefaciens*.

In still another embodiment of the present invention, since green tea extract is known to have antimicrobial activity against several micro-organisms that are harmful to human health at minimum inhibitory concentration or MIC at 250 µg/ml to 1000 µg/ml, it was presumed that crude leaf extract could be used to kill overgrowing *Agrobacterium tumefaciens* during genetic transformation.

In still another embodiment of the present invention, this property of crude leaf extract can be successfully employed to overcome the serious problems of *Agrobacterium tumefaciens* overgrowth and also in preventing the loss of the transformants due to ineffective bactericidal antibiotics such as carbenicillin, cefatoxime, tricaricillin that are generally used in genetic transformation experiments in order to kill overgrowing *Agrobacterium tumefaciens*. Use of crude tea leaf extract for genetic transformation in plants not only has the potential of providing abundantly available natural source of bactericidal agent but is also effective in cutting down the cost of commercially used antibiotics. Moreover, since the crude extracts are also obtained from the maintenance foliage leaves that are generally discarded and burnt, this method appears to be all the more economical and cost effective. Use of crude tea leaf extract is specially important in increasing the transformation efficiency because even the explants or plant species requiring long periods of co-cultivation can be recovered by killing the *Agrobacterium tumefaciens*.

In still another embodiment of the present invention, different explants like leaf, somatic embryo, callus and zygotic axes of tea were used using crude leaf extract of tea cultivars assamica and chinary instead of generally used antibiotics for transgenic production following the methods outlined in Example.

In still another embodiment of the present invention, different explants of different plant species like carnation and rose leaf, somatic embryo, callus were used during genetic transformation using crude leaf extract following the methods outlined in Example 1.

In still another embodiment of the present invention, different concentrations of filter sterilized and autoclaved de-caffeinated fractions of catechin were added as above for the production of transgenics instead of generally used antibiotics like carbenicillin, cefatoxime, tricaricillin etc. following the methods outlined in example 1.

In still another embodiment of the present invention, different concentrations of D-catechin of *Acacia* species were used as mentioned above instead of generally used antibiotics like carbenicillin, cefatoxime, tricaricillin wherein D-catechin was found to promote and not inhibit the growth of *Agrobacterium tumefaciens*.

In further embodiment of the present invention, applicant has claimed an extract as a potent bactericidal agent for *Agrobacterium tumefaciens* mediated genetic transformations comprising of steps (i) inoculation of two strains of *Agrobacterium tumefaciens* viz. EHA105 (mild) and GV2260 (virulent) harbouring the antibiotic resistance genes for kanamycin or hygromycin and the reporter gus gene from mother cultures of respective strains into 10–30 ml liquid modified Yeast Mannitol Broth with kanamycin or hygromycin (ii) incubation for 12–16 hr at 25–30° C. and 150–200 rpm in dark (iii) harvesting at 0.6–0.8 optical density at 600 nm for $1\times10^9$ cells/ml during log phase of bacterial growth (iv) pelleting of living bacterial cells by centrifugation at 15–30 minutes at 4000–8000 rpm and 25–30° C. (v) suspension of bacterial pellet in fresh 5–25 ml of Yeast Mannitol Broth without damaging the bacterial cells (vi) optimization of bacterial cell density at $1\times10^9$ cells/ml by measuring optical density at 600 nm (vii) immersion of various explants of different plants in bacterial suspension for 5–35 minutes (viii) blotting of explants on filter papers to remove excess *Agrobacterium tumefaciens* (ix) incubation of explants on incubation medium for different periods of 1–10 days (x) preparation of crude extract of tea leaf to be used as a bactericidal agent by drying 100–500 g fresh tea leaves of Kangra jat in an oven at 60° C. (xi) overnight extraction of dried leaves at room temperature with 0.4–1.2 liters of 10–40% aqueous acetone and filteration (xii) extraction of the filtrate with 100–500 ml of n-hexane to obtain two layers for removal of lipids (xiii) the aqueous layer taken and concentrated to dryness using standard rotary evaporators (xiv) concentrated extract diluted with water to 10–50 ml and total catechins and caffeine estimated (xv) the aqueous extract served as a crude mixture (xvi) transfer of various explants of different plants to regeneration medium containing different concentrations of 0–600 μg/ml crude tea extract and catechin and caffeine fractions separately for totally killing the residual *Agrobacterium tumefaciens* and for eliminating the problem of polyphenol oxidation in the explants in order to maintain the regeneration potential of explants (xvii) transfer of *Agrobacterium tumefaciens* free explants to regeneration medium containing selection antibiotics for further regeneration and transgenic plant development (xviii) optimization of the concentration and fractions of tea leaf extract on the growth curve of *Agrobacterium tumefaciens* in both solid and liquid Yeast Mannitol Broth media in order to determine the optimum concentration for desired bactericidal activity as well as for promoting regeneration potential of the explant.

In still another embodiment of the present invention, wherein two strains of *Agrobacterium tumefaciens* viz. EHA105 (mild) and GV2260 (virulent) harbouring the antibiotic resistance genes for kanamycin or hygromycin and the reporter gus gene from mother cultures of respective strains were inoculated into 10–30 ml liquid modified Yeast Mannitol Broth with kanamycin or hygromycin.

In still another embodiment of the present invention, wherein the above *Agrobacterium tumefaciens* cultures were harvested at 0.6–0.8 optical density at 600 nm for $1\times10^9$ cells/ml during log phase of bacterial growth.

In still another embodiment of the present invention, wherein bacterial pellet was suspended in fresh 5–25 ml of Yeast Mannitol Broth without damaging the bacterial cells.

In still another embodiment of the present invention, wherein bacterial cell density was optimized at $1\times10^9$ cells/ml by measuring optical density at 600 nm.

In still another embodiment of the present invention, wherein dried leaves overnight extracted at room temperature with 0.4–1.2 liters of 10–40% aqueous acetone and filtered and the filtrate extracted with 100–500 ml of n-hexane to obtain two layers for removal of lipids.

In still another embodiment of the present invention, wherein concentrated extract was diluted with water to 10–50 ml and total catechins and caffeine estimated.

In still another embodiment of the present invention, wherein the aqueous extract served as a crude mixture.

In still another embodiment of the present invention, wherein various explants of different plants were transferred to regeneration medium containing different concentrations of 0–600 μg/ml crude tea extract and catechin and caffeine fractions separately for totally killing the residual *Agrobacterium tumefaciens* and for eliminating the problem of polyphenol oxidation in the explants in order to maintain the regeneration potential of explants the cultures containing crude tea leaf extract were maintained at 25–30° C. in dark at 150–200 rpm for 48 hr.

In still another embodiment of the present invention, wherein the crude leaf extract having bactericidal properties can be obtained in abundance from even the lower maintenance foliage thereby making it more economical as generally such leaves are discarded or burnt.

In still another embodiment of the present invention, wherein the crude leaf extract can also be used as a bactericidal agent for other contaminating bacteria in different in vitro systems involving different plants or explants.

In still another embodiment of the present invention, wherein the crude leaf extract can be used to increase the transformation efficiency considerably by decreasing the mortality rate of transformants due to *Agrobacterium* overgrowth.

The following examples are given by way of illustration and therefore should be construed to limit the scope of the present invention.

EXAMPLE-1

Two strains of *Agrobacterium tumefaciens* viz. EHA105 (mild) and GV2260 (virulent) harbouring the antibiotic resistance genes for kanamycin or hygromycin and the reporter gus gene were inoculated from mother cultures of respective strains into 10–30 ml liquid modified Yeast Mannitol Broth with kanamycin or hygromycin. The cultures were incubated for 12–16 hr at 25–30° C. and 150–200 rpm in dark and harvested at 0.6–0.8 optical density at 600 nm for 1×10⁹ cells/ml during log phase of bacterial growth. The living bacterial cells were pelleted by centrifugation at 15–30 minutes at 4000–8000 rpm and 25–30° C. and suspended in fresh 5–25 ml of Yeast Mannitol Broth without damaging the bacterial cells. The bacterial cell density at 1×10⁹ cells/ml was optimized by measuring optical density at 600 nm.

Various explants of different plants were immersed in bacterial suspension for 5–35 minutes and blotted on filter papers to remove excess *Agrobacterium tumefaciens*. The explants were incubated on incubation medium for different periods of 1–10 days. Crude extract of tea leaf was prepared to be used as a bactericidal agent by drying 100–500 g fresh tea leaves of Kangra jat in an oven at 60° C. Dried leaves were extracted overnight at room temperature with 0.4–1.2 liters of 10–40% aqueous acetone and filtered. The filtrate extracted with 100–500 ml of n-hexane to obtain two layers for removing lipids and the aqueous layer concentrated to dryness using standard rotary evaporators and diluted with water to 10–50 ml.

Total catechins and caffeine estimated and the aqueous extract served as a crude mixture. Various explants of different plants were transferred to regeneration medium containing different concentrations of 0–600 μg/ml crude tea extract for totally killing the residual *Agrobacterium tumefaciens* and for eliminating the problem of polyphenol oxidation in the explants in order to maintain the regeneration potential of explants.

The *Agrobacterium tumefaciens* free explants were transferred to regeneration medium containing kanamycin or hygromycin for further regeneration and transgenic plant development. Concentrations and fractions of tea leaf extract were tested on the growth curve of *Agrobacterium tumefaciens* in both solid and liquid Yeast Mannitol Broth media in order to determine the optimum concentration for desired bactericidal activity as well as for promoting regeneration potential of the explant.

EXAMPLE-2

Two strains of *Agrobacterium tumefaciens* viz. EHA105 (mild) and GV2260 (virulent) harbouring the antibiotic resistance genes for kanamycin or hygromycin and the reporter gus gene were inoculated from mother cultures of respective strains into 10–30 ml liquid modified Yeast Mannitol Broth with kanamycin or hygromycin. The cultures were incubated for 12–16 hr at 25–30° C. and 150–200 rpm in dark and harvested at 0.6–0.8 optical density at 600 nm for 1×10⁹ cells/ml during log phase of bacterial growth. The living bacterial cells were pelleted by centrifugation at 15–30 minutes at 4000–8000 rpm and 25–30° C. and suspended in fresh 5–25 ml of Yeast Mannitol Broth without damaging the bacterial cells. Measurement of optical density at 600 nm at regular 6 hr intervals for 0–48 hr and the mean of three readings were plotted for development of the growth curve.

Crude mixture of catechins as well as caffeine at concentrations of 2–600 μg/ml were added to fresh cultures of *Agrobacterium tumefaciens* and maintained at 25–30° C. in dark at 150–200 rpm for 48 hr. The optical density was again measured at regular interval of 6 hr each for 0–48 hr for the plotting of the mean of the three readings in a linear graph in order to determine the effect of the crude mixture of catechins as well as caffeine at concentrations of 2–600 μg/ml on fresh cultures of *Agrobacterium tumefaciens*.

EXAMPLE-3

Single colony of *Agrobacterium tumefaciens* was streaked on agar solidified plates containing different concentrations 2–600 μg/ml of crude tea leaf extract containing mixture of catechins and caffeine in order to determine its bactericidal effect on agar solidified media by incubating the plates at 25–30° C. in dark for 12–16 hr.

Advantages of the Present Invention

1. The main advantage of the present invention is that its an efficient and cost effective method of preventing growth of genetic transformant bacteria *Agrobacterium tumefaciens* after transformation in plants by using tea leaf extract as a bactericide.

2. Another advantage of the instant application is that it's a method for enhanced genetic transformation in plant systems using bacteria *Agrobacterium tumefaciens* as the transformant.

3. Yet another advantage of the present invention is that it's a method for prevention of overgrowth of genetic transformant of plants wherein the growth of the plant after transformation is normal with no polyphenol oxidation.

4. Still another advantage is a method wherein, crude tea leaf extract can be used as a potent bactericidal agent for *Agrobacterium tumefaciens* mediated genetic transformations as it can be used for killing the overgrowth of *Agrobacterium tumefaciens* in systems or plants or explants requiring longer co-cultivation periods thereby increasing the transformation efficiency.

5. Still another advantage is a method wherein, crude tea leaf extract can be used for *Agrobacterium tumefaciens* mediated genetic transformation in different systems or plants or explants wherein the generally used bactericidal antibiotics are ineffective.

6. Still another advantage is a method wherein, since no commercial bactericidal antibiotics need to be used, crude tea leaf extract prove to be a cost effective system for *Agrobacterium tumefaciens* mediated genetic transformation.

7. Still another advantage is a method wherein, since the crude leaf extract with bactericidal activity is obtained without involving any expensive instruments or costly extraction methods, its use proves to be an economical method.

8. Still another advantage is a method wherein, the crude leaf extract with bactericidal activity can be easily obtained in abundance from naturally growing tea bushes round the year.

9. Still another advantage is a method wherein, the crude leaf extract as a bactericidal agent is of natural origin and is not of synthetic or semi-synthetic nature.

10. Still another advantage is a method wherein, the crude leaf extract as a bactericidal agent can be obtained in abundance from even the lower maintenance foliage thereby making it more economical as generally such leaves are discarded or burnt.

11. Still another advantage is a method wherein, the crude leaf extract can also be used as a bactericidal agent for other contaminating bacteria in different in vitro systems involving different plants or explants.

12. Still another advantage is a method wherein, the crude tea leaf extract can also be used during 'hairy root production' using *Agrobacterium rhizogenesis*.

13. Still another advantage is a method wherein, the crude leaf extract can be used to increase the transformation efficiency considerably by decreasing the mortality rate of transformants due to *Agrobacterium* overgrowth.

The invention claimed is:

1. A method of inhibiting growth of genetic transformant bacteria *Agrobacterium tumefaciens* after transformation in plants selected from the group consisting of tea, carnations, and roses, said method comprising:
   (1) inoculating *Agrobacterium tumefaciens* bacteria strains EHA105 and GV2260 harbouring antibiotic resistant genes for *kanamycin* and/or hygromycin and a reporter gus gene from mother cultures of said respective strains into a liquid-modified yeast mannitol broth with kanamycin and/or hygromycin, thereby forming a culture comprising said bacteria at a concentration of from 10 to 75 micrograms/ml;
   (2) incubating the culture in darkness for a time duration of 10–20 hours at a temperature of 20–35° C. and at a revolution rate of 100–300 rpm;
   (3) after said incubation, harvesting the culture at 0.6–0.8 optical density at 600 nm for concentration of $1 \times 10^9$ cells/ml during log phase of bacterial growth;
   (4) pelleting live bacterial cells in the harvested culture by centrifuging the harvested culture for a time duration of 15–40 minutes at a revolution rate of 3000–9000 rpm and at a temperature of 20–35° C., thereby forming a pellet;
   (5) suspending the pellet in a fresh yeast mannitol broth medium to form a bacterial suspension;
   (6) optimizing bacterial cell density at $1 \times 10^9$ cells/ml of the bacterial suspension by measuring optical density at 600 nm after about every 6 hours interval to estimate growth rate of the bacteria spectrophotometrically, wherein optimization of cell density has an optical density ranging between 0.6 and 0.8 at 600 nm at $1 \times 10^9$ cells/ml;
   (7) immersing one or more explants of one or more plants in the bacterial suspension for a time duration of from 3 to 40 minutes, the explants being selected from the group consisting of leaf, somatic embryo, callus and zygotic axes;
   (8) removing excess genetic transformant *Agrobacterium tumefaciens* bacteria from said one or more explants;
   (9) incubating the explants obtained in step (8) in an incubation medium for a time duration of from 1 to 20 days;
   (10) preparing a crude extract of tea by a process comprising:
      (a) drying fresh tea leaves of Kangra jat in an oven at a temperature of from 50° C. to 700° C.;
      (b) combining the dried fresh tea leaves with a 10–40% aqueous acetone to form a leaves/acetone solution and subjecting said dried fresh tea leaves to overnight extraction at room temperature with the aqueous acetone to form an extract, the dried fresh leaves being present in the leaves/acetone solution at a concentration of from 200 to 500 grams/liter, and the acetone being present in the leaves/acetone solution at a concentration of from 5 to 50%;
      (c) filtering the extract to form a filtrate;
      (d) extracting the filtrate with n-hexane to obtain an aqueous layer and a lipid layer; the ratio of acetone or n-hexane during extraction being from 4:5 to 12:1;
      (e) concentrating the aqueous layer to dryness; and
      (f) diluting the concentrated aqueous layer with water to obtain said crude tea extract, the crude tea extract comprising catechins and caffeine at a concentration of from 2 to 750 micrograms/ml;
   (11) transferring the one or more explants of step (9) to a regeneration medium containing from 1 to 1000 micrograms/ml of the crude tea extract prepared in step (10); and
   (12) maintaining the one or more explants in said regeneration medium in darkness at 25–30° C. at 150–200 rpm for 48 hours, thereby obtaining one or more explants upon which growth of genetic transformant bacteria *Agrobacterium tumefaciens* is inhibited.

2. A method as claimed in claim 1, wherein said tea extract eliminates polyphenol oxidation during transformation.

3. A method as claimed in claim 1, wherein said one or more explants show normal growth after incubation with said crude tea extract in step (12).

4. method as claimed in claim 1, wherein cell density is measured spectrophotometrically.

5. A method as claimed in claim 1, wherein in step (8) said excess genetic transformant *Agrobacterium tumefaciens* bacteria is removed from said one or more explants by blotting said one or more explants on filter paper.

6. A method as claimed in claim 1, wherein in step (10)(a), the fresh tea leaves are dried in an oven at a temperature of 60° C.

7. A method as claimed in claim 1, wherein in step (10)(e), said aqueous layer is concentrated to dryness using rotary evaporators.

8. A method as claimed in claim 1, wherein in step (2), said culture is incubated for a time duration of 12–16 hours at a temperature of 25–30° C. and at a revolution rate of 150–200 rpm.

9. A method as claimed in claim 1, wherein in step (4), the harvest is pelleted by centrifuging at 4000–8000 rpm for a time duration of 15 to 30 minutes and at a temperature of 25–30° C.

10. A method as claimed in claim 1, wherein said culture is centrifuged at a temperature ranging between 25 to 30° C.

11. A method as claimed in claim 1, wherein in step (7), the one or more explants are immersed in the bacterial suspension for a time duration of from 5 to 35 minutes.

12. A method as claimed in claim 1, wherein in step (10)(b), the dried fresh tea leaves are combined with from 0.4 to 1.2 liters of the aqueous acetone.

13. A method as claimed in claim 1, wherein in step (10)(d), the filtrate is extracted with 100–500 ml of the n-hexane.

14. A method as claimed in claim 1, wherein in step (10)(f), the concentrated aqueous layer is diluted with water to 10–50 ml.

* * * * *